(12) United States Patent
Park et al.

(10) Patent No.: US 10,765,688 B2
(45) Date of Patent: Sep. 8, 2020

(54) LIPOLYTIC COMPOSITION CONTAINING PHOSPHOCHOLINE DERIVATIVES

(71) Applicant: PENMIX LTD., Cheonan-si, Chungcheongnam-do (KR)

(72) Inventors: Dongkyu Park, Seoul (KR); Sang Yun Lee, Yongin-si (KR); Young Sub Song, Seoul (KR); Surin Kim, Suwon-si (KR); Joo Hwan Kim, Siheung-si (KR); Ji Hyun Moon, Seoul (KR); Seung Jun Lee, Changwon-si (KR); Hana Lee, Goyang-si (KR); Seung Ho Ji, Yongin-si (KR)

(73) Assignee: PENMIX LTD., Cheonan-si, Chungcheongnam-do (KR)

( * ) Notice: Subject to any disclaimer, the term of this patent is extended or adjusted under 35 U.S.C. 154(b) by 67 days.

(21) Appl. No.: 15/906,451

(22) Filed: Feb. 27, 2018

(65) Prior Publication Data

US 2019/0134068 A1    May 9, 2019

(30) Foreign Application Priority Data

Nov. 3, 2017 (KR) .................. 10-2017-0145750

(51) Int. Cl.
| | | |
|---|---|---|
| *A61K 31/661* | (2006.01) | |
| *A61P 3/04* | (2006.01) | |
| *A61K 31/56* | (2006.01) | |

(52) U.S. Cl.
CPC ............ *A61K 31/661* (2013.01); *A61K 31/56* (2013.01); *A61P 3/04* (2018.01)

(58) Field of Classification Search
CPC .................................................. A61K 31/661
See application file for complete search history.

(56) References Cited

U.S. PATENT DOCUMENTS

| 2005/0143347 A1 | 6/2005 | Boderke et al. |
| 2005/0287199 A1 | 12/2005 | Denney et al. |
| 2010/0004216 A1 | 1/2010 | Boderke et al. |
| 2010/0331281 A1 | 12/2010 | Moore et al. |
| 2016/0339042 A1 | 11/2016 | Modi |

FOREIGN PATENT DOCUMENTS

WO    WO-2009067182 A2  *  5/2009  ........... A61K 31/661

OTHER PUBLICATIONS

Stojancevic et al., Application of bile acids in drug formulation and delivery, 2013, Frontiers in Life Science, vol. 7, Nos. 3-4, pp. 112-122 (Year: 2013).*

* cited by examiner

*Primary Examiner* — Kortney L. Klinkel
*Assistant Examiner* — Tori Strong
(74) *Attorney, Agent, or Firm* — Vorys, Sater, Seymour and Pease LLP; Mih Suhn Koh

(57) ABSTRACT

The present invention provides a composition for lipolysis, for example a pharmaceutical composition for preventing or treating obesity including localized fat deposits (LFD), comprising certain phosphocholine derivatives or pharmaceutically acceptable salt thereof. The pharmaceutical composition of the present invention shows an excellent lipolytic activity as well as a uniform lipolytic activity. And also, the pharmaceutical composition of the present invention can minimize side effects such as inflammation, tissue necrosis, etc., at the administered site. In addition, the pharmaceutical composition of the present invention has excellent storage stability.

9 Claims, 5 Drawing Sheets

LIPOLYTIC COMPOSITION CONTAINING PHOSPHOCHOLINE DERIVATIVES

TECHNICAL FIELD

The present invention relates to a composition for lipolysis, for example a pharmaceutical composition for preventing or treating obesity, comprising a phosphocholine derivative or pharmaceutically acceptable salt thereof.

BACKGROUND ART

Fats are derived from the accumulation of overfed energy in white adipose tissue and the excessive accumulation thereof in white adipose tissue is commonly referred to as obesity. The breakdown of triglycerides into free fatty acid (FFA) and glycerol, e.g., by hormone sensitive lipase (HSL), is referred to as lipolysis.

For improving obesity, a surgical operation, liposuction, is being carried out. Liposuction, which is also known as lipoplasty or liposculpture suction lipectomy, is a cosmetic surgical operation for removing fats from various sites in the body, such as abdomen, thighs, hips, neck, upper arms, and so on. However, there are concerns that liposuction may cause serious side effects, including wounds, swelling, paralysis and burning sensation, a risk of infection in the surgical site; damage to skin or nerves; and puncture wounds in critical organs. In addition, it requires a significant period of time for treatment and recovery; and also there are risks associated with anesthesia because it requires local anesthesia or general anesthesia during the surgical procedure.

Phosphatidylcholines (PC) are a class of phospholipids that incorporate choline as a headgroup. They are widely found in animals, plants, yeast, and fungi and are also referred to as lecithin or unsaturated lecithin. They are mainly contained in the brain, nerves, blood cells, egg yolk and the like in mammals; and in soybeans, sunflower seeds, wheat germ and the like in plants. Because phosphatidylcholine has four double bonds in its molecule, it is easily oxidized during the preparation or during the storage, thereby the structure thereof being deformed. In order to overcome such disadvantage, the saturated lecithin forms have been developed which are prepared by adding hydrogen to the unsaturated lecithin. US Laid-open Patent Publication No. US 2005/0287199 has disclosed a method for reducing adipose tissue which includes injecting lecithin. In addition, US Laid-open Patent Publication No. US 2016/0339042 has disclosed a method for reducing localized adipose tissue comprising topically administering to a site at or proximate adipose tissue a composition comprising lecithin and bile acid or a salt thereof. However, the topical injection of lecithin for inducing lipolysis leads to side effect problems such as erythema, inflammation, tissue necrosis, edema, dimpling and the like. And also, when a lecithin-containing formulation is stored for a long period of time, it leads to problems such as lowered stability and lipolytic activity.

DISCLOSURE

Technical Problem

The present inventors carried out various researches in order to develop a composition for lipolysis, for example a pharmaceutical composition for preventing or treating obesity, which has an excellent lipolytic activity and stability without significant side effects. The present inventors evaluated activities, side effects, and stabilities of various choline derivatives. As the results thereof, the present inventors have found that the formulations containing certain phosphocholine derivatives have a superior and uniform lipolytic activity and stability and can minimize side effects in the administration site such as inflammation, tissue necrosis, etc., in comparison to a conventional phosphatidylcholine-containing formulation.

Therefore, the present invention provides a pharmaceutical composition for preventing or treating obesity comprising said phosphocholine derivatives as an active ingredient.

And also, the present invention provides a method for inducing lipolysis or treating obesity in a mammal in need thereof, comprising administering to the mammal a therapeutically effective amount of said phosphocholine derivatives.

And also, the present invention provides a use of said phosphocholine derivatives for the manufacture of a medicament for inducing lipolysis or preventing or treating obesity.

Technical Solution

In accordance with an aspect of the present invention, there is provided a pharmaceutical composition for preventing or treating obesity, comprising a therapeutically effective amount of a compound of Formula 1 or pharmaceutically acceptable salt thereof as an active ingredient:

<Formula 1>

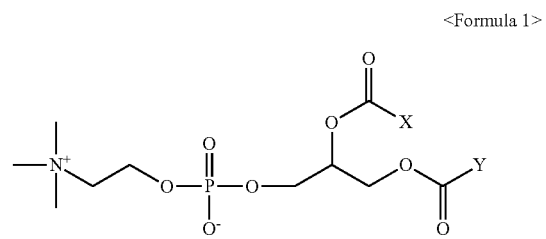

wherein,

X and Y are, independently of each other, a $C_9$~$C_{17}$ alkyl group; or a $C_{15}$~$C_{21}$ alkenyl group having one or two double bonds, with the proviso that X and Y are not a $C_{17}$ alkyl group at the same time; and X and Y are not a $C_{17}$ alkenyl group having two double bonds at the same time.

In the pharmaceutical composition of the present invention, the compound of Formula 1 may be one or more selected from the group consisting of:

1,2-didecanoyl-sn-glycero-3-phosphocholine,
1,2-dilauroyl-sn-glycero-3-phosphocholine,
1,2-dimyristoyl-sn-glycero-3-phosphocholine,
1,2-dipalmitoyl-sn-glycero-3-phosphocholine,
1-myristoyl-2-palmitoyl-sn-glycero-3-phosphocholine;
1-myristoyl-2-stearoyl-sn-glycero-3-phosphocholine,
1-palmitoyl-2-myristoyl-sn-glycero-3-phosphocholine;
1-palmitoyl-2-stearoyl-sn-glycero-3-phosphocholine,
1-stearoyl-2-myristoyl-sn-glycero-3-phosphocholine,
1-stearoyl-2-palmitoyl-sn-glycero-3-phosphocholine,
1,2-dierucoyl-sn-glycero-3-phosphocholine,
1,2-dioleoyl-sn-glycero-3-phosphocholine,
1-palmitoyl-2-oleoyl-sn-glycero-3-phosphocholine; and
1-stearoyl-2-oleoyl-sn-glycero-3-phosphocholine.

Preferably, the compound of Formula 1 may be one or more selected from the group consisting of:

1,2-dimyristoyl-sn-glycero-3-phosphocholine,
1,2-dipalmitoyl-sn-glycero-3-phosphocholine,
1-stearoyl-2-myristoyl-sn-glycero-3-phosphocholine,
1,2-didecanoyl-sn-glycero-3-phosphocholine,
1-palmitoyl-2-stearoyl-sn-glycero-3-phosphocholine; and
1,2-dilauroyl-sn-glycero-3-phosphocholine.

More preferably, the compound of Formula 1 may be 1,2-dimyristoyl-sn-glycero-3-phosphocholine.

The pharmaceutical composition of the present invention may further comprise a therapeutically effective amount of bile acid or pharmaceutically acceptable salt thereof. The bile acid or pharmaceutically acceptable salt thereof may be one or more selected from the group consisting of cholic acid, glycocholic acid, glycodeoxycholic acid, deoxycholic acid, taurocholic acid, ursodeoxycholic acid, tauroursodeoxycholic acid, taurodeoxycholic acid, chenodeoxycholic acid, glycoursodeoxycholic acid, sodium deoxycholate, and sodium taurocholate. Preferably, the bile acid or pharmaceutically acceptable salt thereof may be one or more selected from the group consisting of glycocholic acid, deoxycholic acid, taurocholic acid, tauroursodeoxycholic acid, glycoursodeoxycholic acid, sodium deoxycholate, and sodium taurocholate. In an embodiment, a weight ratio of the compound of Formula 1 or pharmaceutically acceptable salt thereof and the bile acid or pharmaceutically acceptable salt thereof may range from 0.5:1 to 40:1.

The pharmaceutical composition of the present invention may be formulated into a formulation for parenteral administration. The formulation for parenteral administration may be a formulation for transdermal administration, a formulation for subcutaneous administration, a formulation for intramuscular administration, or a formulation for intraperitoneal administration. And also, the formulation for parenteral administration may be in the form of a liquid formulation or a dry powder formulation; preferably in the form of a solution, an emulsion, or a lyophilized powder. The formulation for parenteral administration may comprise one or more pharmaceutically acceptable excipients selected from the group consisting of a pH controlling agent, an isotonic agent, a surfactant, a stabilizer, a preservative, a chelating agent, a buffer, and a cryoprotectant; and one or more pharmaceutically acceptable carriers selected from the group consisting of an oil, an organic solvent, and an aqueous solvent.

In accordance with another aspect of the present invention, there is provided a method for inducing lipolysis or treating obesity in a mammal in need thereof, comprising administering to the mammal a therapeutically effective amount of the compound of Formula 1 or pharmaceutically acceptable salt thereof.

In the method of the present invention, the compound of Formula 1 may be one or more selected from the group consisting of:
1,2-didecanoyl-sn-glycero-3-phosphocholine,
1,2-dilauroyl-sn-glycero-3-phosphocholine,
1,2-dimyristoyl-sn-glycero-3-phosphocholine,
1,2-dipalmitoyl-sn-glycero-3-phosphocholine,
1-myristoyl-2-palmitoyl-sn-glycero-3-phosphocholine;
1-myristoyl-2-stearoyl-sn-glycero-3-phosphocholine,
1-palmitoyl-2-myristoyl-sn-glycero-3-phosphocholine;
1-palmitoyl-2-stearoyl-sn-glycero-3-phosphocholine,
1-stearoyl-2-myristoyl-sn-glycero-3-phosphocholine,
1-stearoyl-2-palmitoyl-sn-glycero-3-phosphocholine,
1,2-dierucoyl-sn-glycero-3-phosphocholine,
1,2-dioleoyl-sn-glycero-3-phosphocholine,
1-palmitoyl-2-oleoyl-sn-glycero-3-phosphocholine; and
1-stearoyl-2-oleoyl-sn-glycero-3-phosphocholine.

Preferably, the compound of Formula 1 may be one or more selected from the group consisting of:
1,2-dimyristoyl-sn-glycero-3-phosphocholine,
1,2-dipalmitoyl-sn-glycero-3-phosphocholine,
1-stearoyl-2-myristoyl-sn-glycero-3-phosphocholine,
1,2-didecanoyl-sn-glycero-3-phosphocholine,
1-palmitoyl-2-stearoyl-sn-glycero-3-phosphocholine; and
1,2-dilauroyl-sn-glycero-3-phosphocholine.

More preferably, the compound of Formula 1 may be 1,2-dimyristoyl-sn-glycero-3-phosphocholine.

In accordance with still another aspect of the present invention, there is provided a use of the compound of Formula 1 or pharmaceutically acceptable salt thereof for the manufacture of a medicament for inducing lipolysis or preventing or treating obesity.

In the use of the present invention, the compound of Formula 1 may be one or more selected from the group consisting of:
1,2-didecanoyl-sn-glycero-3-phosphocholine,
1,2-dilauroyl-sn-glycero-3-phosphocholine,
1,2-dimyristoyl-sn-glycero-3-phosphocholine,
1,2-dipalmitoyl-sn-glycero-3-phosphocholine,
1-myristoyl-2-palmitoyl-sn-glycero-3-phosphocholine;
1-myristoyl-2-stearoyl-sn-glycero-3-phosphocholine,
1-palmitoyl-2-myristoyl-sn-glycero-3-phosphocholine;
1-palmitoyl-2-stearoyl-sn-glycero-3-phosphocholine,
1-stearoyl-2-myristoyl-sn-glycero-3-phosphocholine,
1-stearoyl-2-palmitoyl-sn-glycero-3-phosphocholine,
1,2-dierucoyl-sn-glycero-3-phosphocholine,
1,2-dioleoyl-sn-glycero-3-phosphocholine,
1-palmitoyl-2-oleoyl-sn-glycero-3-phosphocholine; and
1-stearoyl-2-oleoyl-sn-glycero-3-phosphocholine.

Preferably, the compound of Formula 1 may be one or more selected from the group consisting of:
1,2-dimyristoyl-sn-glycero-3-phosphocholine,
1,2-dipalmitoyl-sn-glycero-3-phosphocholine,
1-stearoyl-2-myristoyl-sn-glycero-3-phosphocholine,
1,2-didecanoyl-sn-glycero-3-phosphocholine,
1-palmitoyl-2-stearoyl-sn-glycero-3-phosphocholine; and
1,2-dilauroyl-sn-glycero-3-phosphocholine.

More preferably, the compound of Formula 1 may be 1,2-dimyristoyl-sn-glycero-3-phosphocholine.

Advantageous Effects

The pharmaceutical composition of the present invention comprising certain phosphocholine derivatives, i.e., the compound of Formula 1 or pharmaceutically acceptable salt thereof shows not only an excellent lipolytic activity but also uniformity in its lipolytic activity in comparison to a conventional phosphatidylcholine-containing formulation. And also, the pharmaceutical composition of the present invention can minimize side effects such as inflammation, tissue necrosis, etc., in the administration site. In addition, the pharmaceutical composition of the present invention has excellent storage stability. Accordingly, the pharmaceutical composition of the present invention can inhibit non-uniform arrangement of subcutaneous fats and aesthetic damages derived therefrom; and therefore can be usefully applied for preventing or treating obesity, especially localized fat deposits (LFD).

DESCRIPTION OF DRAWINGS

In FIG. 4, the smaller red oil size represents better lipolysis.

BEST MODE

Figure 1:
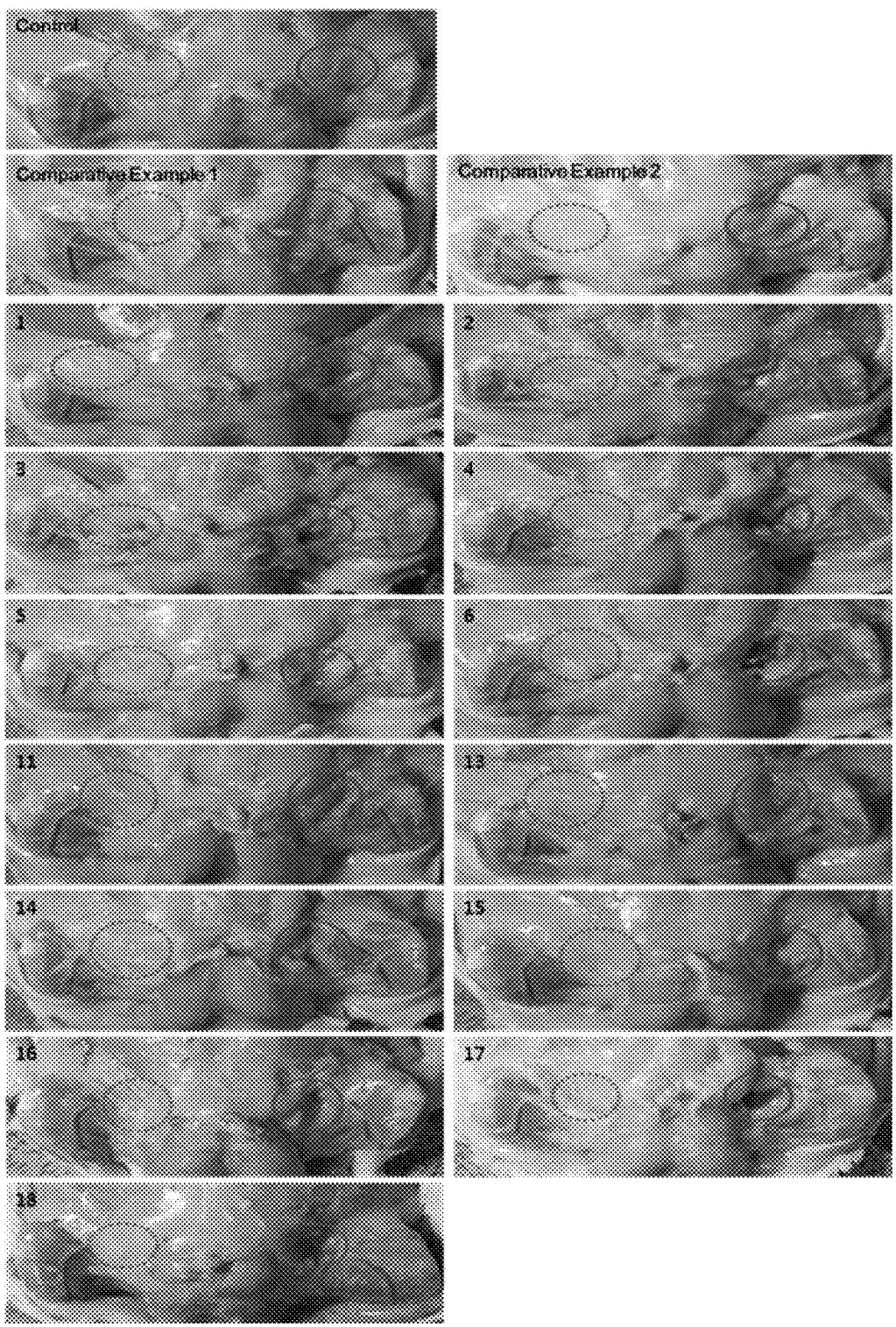
FIGS. 1 and 2 show the results obtained from observing the lipolytic activities at the non-administration site (dotted circle) and at the administration site (dark circle) of the rats administered with the formulations of the present invention, the formulations of Comparative Examples, and the vehicle.

The phosphocholine derivatives according to the present invention have an excellent and uniform lipolytic activity and can minimize side effects such as inflammation, tissue necrosis, etc., at the administered site; and therefore can be usefully applied for preventing or treating obesity, especially localized fat deposits (LFD). Therefore, the present invention provides a pharmaceutical composition for preventing or treating obesity, comprising said phosphocholine derivatives as an active ingredient. Specifically, the present invention provides a pharmaceutical composition for preventing or treating obesity, comprising a therapeutically effective amount of a compound of Formula 1 or pharmaceutically acceptable salt thereof as an active ingredient:

<Formula 1>

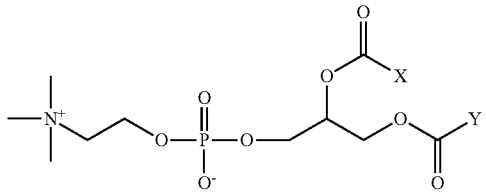

wherein,

X and Y are, independently of each other, a $C_9$~$C_{17}$ alkyl group; or a $C_{15}$~$C_{21}$ alkenyl group having one or two double bonds, with the proviso that X and Y are not a $C_{17}$ alkyl group at the same time; and X and Y are not a $C_{17}$ alkenyl group having two double bonds at the same time.

Preferably, in the pharmaceutical composition of the present invention, the compound of Formula 1 may be one or more selected from the group consisting of:

1,2-didecanoyl-sn-glycero-3-phosphocholine (DDPC),
1,2-dilauroyl-sn-glycero-3-phosphocholine (DLPC),
1,2-dimyristoyl-sn-glycero-3-phosphocholine (DMPC),
1,2-dipalmitoyl-sn-glycero-3-phosphocholine (DPPC),
1-myristoyl-2-palmitoyl-sn-glycero-3-phosphocholine (MPPC),
1-myristoyl-2-stearoyl-sn-glycero-3-phosphocholine (MSPC),
1-palmitoyl-2-myristoyl-sn-glycero-3-phosphocholine (PMPC);
1-palmitoyl-2-stearoyl-sn-glycero-3-phosphocholine (PSPC);
1-stearoyl-2-myristoyl-sn-glycero-3-phosphocholine (SMPC),
1-stearoyl-2-palmitoyl-sn-glycero-3-phosphocholine (SPPC);
1,2-dierucoyl-sn-glycero-3-phosphocholine (DEPC);
1,2-dioleoyl-sn-glycero-3-phosphocholine (DOPC);
1-palmitoyl-2-oleoyl-sn-glycero-3-phosphocholine (POPC); and
1-stearoyl-2-oleoyl-sn-glycero-3-phosphocholine (SOPC).

More preferably, in the pharmaceutical composition of the present invention, the compound of Formula 1 may be one or more selected from the group consisting of:

1,2-dimyristoyl-sn-glycero-3-phosphocholine (DMPC);
1,2-dipalmitoyl-sn-glycero-3-phosphocholine (DPPC);
1-stearoyl-2-myristoyl-sn-glycero-3-phosphocholine (SMPC),
1,2-didecanoyl-sn-glycero-3-phosphocholine (DDPC);
1-palmitoyl-2-stearoyl-sn-glycero-3-phosphocholine (PSPC); and
1,2-dilauroyl-sn-glycero-3-phosphocholine (DLPC).

Most preferably, in the pharmaceutical composition of the present invention, the compound of Formula 1 may be 1,2-dimyristoyl-sn-glycero-3-phosphocholine (DMPC).

The compounds of Formula 1 or salt thereof, which are known compounds, may be prepared according to known methods. For example, the compound of Formula 1 or salt thereof may be prepared by hydrolyzing and purifying soy bean lecithin to obtain glycero phosphocholine; and then reacting the glycero phosphocholine with a fatty acid such as myristic acid. And also, the compound of Formula 1 or salt thereof can be purchased as it is commercially available (for example, Sigma-Aldrich).

The compound of Formula 1 or pharmaceutically acceptable salt thereof may have substituents containing asymmetric carbon and therefore be in the form of racemic mixture (RS) or in forms of optical isomers, such as (R) or (S) isomer. Therefore, the compound of Formula 1 or pharmaceutically acceptable salt thereof comprises both racemic mixture (RS) and optical isomers such as (R) or (S) isomer unless described otherwise.

The compound of Formula 1 of the present invention may be in a pharmaceutically acceptable salt form. The salt may be an acid addition salt form, which includes e.g., salts derived from an inorganic acid such as hydrochloric acid, hydrobromic acid, sulfuric acid, phosphoric acid, nitric acid, or carbonic acid; and salts derived from an organic acid such as citric acid, acetic acid, lactic acid, tartaric acid, maleic acid, fumaric acid, lactobionic acid, salicylic acid, malonic acid, formic acid, propionic acid, oxalic acid, trifluoroacetic acid, benzoic acid, gluconic acid, methanesulfonic acid, glycolic acid, succinic acid, p-toluenesulfonic acid, glutamic acid, or aspartic acid, but not limited thereto. And also, the salt includes an alkali metal salt such as lithium salt, sodium salt, or potassium salt; an alkaline earth metal salt such as calcium salt or magnesium salt; or a chromium salt.

The pharmaceutical composition of the present invention may further comprise a therapeutically effective amount of bile acid or pharmaceutically acceptable salt thereof as an active ingredient, in addition to the compound of Formula 1 or pharmaceutically acceptable salt thereof. The bile acid may be one or more selected from the group consisting of cholic acid, glycocholic acid, glycodeoxycholic acid, deoxycholic acid, taurocholic acid, ursodeoxycholic acid, tauroursodeoxycholic acid, taurodeoxycholic acid, chenodeoxycholic acid, glycoursodeoxycholic acid, sodium deoxycholate, and sodium taurocholate. Preferably, the bile acid or pharmaceutically acceptable salt thereof may be one or more selected from the group consisting of glycocholic acid, deoxycholic acid, taurocholic acid, tauroursodeoxycholic acid, glycoursodeoxycholic acid, sodium deoxycholate, and sodium taurocholate. More preferably, the bile acid or pharmaceutically acceptable salt thereof may be one or more selected from the group consisting of glycocholic acid, deoxycholic acid, tauroursodeoxycholic acid, sodium deoxycholate, and sodium taurocholate. Most preferably, the bile acid or pharmaceutically acceptable salt thereof may be glycocholic acid or its salt (e.g., sodium salt) or taurocholic acid or its salt (e.g., sodium salt). When the pharmaceutical composition of the present invention further comprises a therapeutically effective amount of bile acid or pharmaceutically acceptable salt thereof as an active ingredient, in addition to the compound of Formula 1 or pharmaceutically acceptable salt thereof, a weight ratio of the compound of Formula 1 or pharmaceutically acceptable salt thereof and the bile acid or pharmaceutically acceptable salt thereof may range from 0.5:1 to 40:1, preferably from 1:1 to 35:1, more preferably from 1:1 to 20:1, still more preferably range from 1:1 to 10:1, in order to minimize side effects such as inflammation, tissue necrosis, etc. and to provide effective lipolysis.

The composition of the present invention may be administered parenterally, more preferably, topically administered through parenteral route. The topical administration includes topical application(s) to the regions such as under-eye, under-chin, under-arm, hip, calf, back, thigh, ankle, abdomen, and the like. For example, the composition of the present invention may be formulated into a formulation for parenteral administration (including a formulation for topical administration); and the formulation for parenteral administration may be a formulation for transdermal administration, subcutaneous administration, intramuscular administration, or intraperitoneal administration. And also, the formulation for parenteral administration may be a formulation for single administration or multiple administrations. The formulation for multiple administrations may be prepared to be suitable for administering in a volume of about 0.5 ml at least once a day at intervals of 3 to 14 days. If necessary, the formulation for multiple administrations may be repeatedly administered to separated parts at a distance of 0.5 to 2.0 cm.

The formulation for parenteral administration may be in the form of a liquid formulation or a dry powder formulation. The liquid formulation includes a solution, an emulsion, a suspension, and the like, preferably in the form of solutions or emulsions. The liquid formulation may be sterile-filtered with a bacterial filter or the like and then filled into an ampule or a vial. The dry powder formulation includes a power form obtained by drying a solution, an emulsion, a suspension and the like through conventional drying methods such as rotary evaporation drying, spray drying, fluidized bed drying, and freeze drying (lyophilization), preferably through freeze drying. The dry powder formulation may be diluted with water for injection, sterile distilled water, water for injection, physiological saline, a glucose solution, a glucose injection, a xylitol injection, a D-mannitol injection, a fructose injection, a Dexran-40 injection, a Dexran-70 injection, an amino acid injection, a Ringer's solution, a lactated Ringer's solution, and the like, before administering to a subject.

The formulation for parenteral administration in the form of a liquid formulation or a dry powder formulation may be prepared according to the conventional methods used in the field of pharmaceutics, using pharmaceutically acceptable excipients and/or carriers. Therefore, the pharmaceutical composition may comprise one or more pharmaceutically acceptable excipients selected from the group consisting of a pH controlling agent, an isotonic agent, a surfactant, a stabilizer, a preservative (or an antimicrobial agent), a chelating agent, a buffer, and a cryoprotectant; and one or more pharmaceutically acceptable carriers selected from the group consisting of an oil, an organic solvent, and an aqueous solvent.

The pH controlling agent includes a pH controlling agent conventionally used in a formulation for injection, for example, sodium hydroxide, citric acid, acetic acid, phosphoric acid, gluconic acid, ascorbic acid, succinic acid and the lie, but not limited thereto. The pharmaceutical composition of the present invention may have a pH ranging from pH 3 to pH 9, preferably a pH ranging from pH 5 to pH 8. The pharmaceutical composition having said pH range may minimize pain and/or inflammation when it is topically administered.

The isotonic agent includes a sugar, a sugar alcohol, a salt, and the like, for example glucose, glycerin, sodium chloride, calcium chloride, sodium sulfate, glycerin, propylene glycol, polyethylene glycol (e.g., polyethylene glycol having 1000 or less of molecular weight), dextrose, hydroxypropyl betadex, mannitol, potassium chloride, dextran, ficoll, gelatin, hydroxyethyl starch, and the like, but not limited thereto. In an embodiment, the isotonic agent may be glycerin and/or sodium chloride. Especially, glycerin may also help improve stability of the formulation. The isotonic agent may be used in an amount suitable for providing a physiologically acceptable osmolality.

The surfactant includes ionic, non-ionic, and/or amphoteric surfactants. In an embodiment, the surfactant may be a non-ionic surfactant. The non-ionic surfactant includes for example polyoxyethylene sorbitan fatty acid ester (e.g., Tween series surfactants), polyoxyethylene polyoxypropylene block copolymer (e.g., Poloxamer series surfactants), and the like, but not limited thereto.

The stabilizer includes for example cholesterol, β-cholesterol, sitosterol, ergosterol, stigmasterol, stigmasterol acetate, lanosterol, and a combination thereof, but not limited thereto. In an embodiment, the stabilizer may be cholesterol.

The preservative includes antimicrobial agents conventionally used in the field of pharmaceutics. The preservative includes benzyl alcohol, glycerin, m-cresol, phenol, benzalkonium chloride, benzethonium chloride, acacia, albumin, alcohol, alginic acid, ascorbyl palmitate, aspartame, boric acid, citric acid, glycerin, pentetic acid, sodium acetate, sorbic acid, chlorobutanol, o-cresol, p-cresol, chlorocresol, phenylmercuric nitrate, thimerosal, benzoic acid, cholesterol, and the like, but not limited thereto. In an embodiment, the preservative may be benzyl alcohol and/or glycerin.

The chelating agent includes ethylenediaminetetraacetic acid (EDTA), buthylenediaminetetraacetic acid, cyclohexane-1,2-diaminetetraacetic acid (CyDTA), diethylenetriaminepentaacetic acid (DETPA), ethylenediaminetetrapropionic acid, (hydroxyethyl)ethylenediaminetriacetic acid (HEDTA;), ethylenediaminetetra(methylenephosphonic acid (EDTMP), triethylenetetraminehexaacetic acid (TTHA), 1,3-diamino-2-hydroxypropane-N,N,N',N'-tetracetic acid (DHPTA), methyliminodiacetic acid, propylenediaminetetracetic acid, 1,5,9-triazacyclodecane-N,N',N''-tris (methylenephosphonic acid (DOTRP), 1,4,7,10-tetraazacyclodecane-N,N', N'',N'''-tetrakis (methylenephosphonic acid (DOTP), nitrilotris(methylene) triphosphonic acid, diethylenetriaminephenta (methylenephosphonic acid (DETAP), aminotri (methylenephosphonic acid, 1-hydroxyethylene-1,1-diphosphonic acid, bis(hexamethylene)triaminephosphonic acid, 1,4,7-triazacyclononan-N,N',N''-tris(methylenephosphonic acid (NOTP), 2-phophonobuthan-1,2,4-tricarboxylic acid, nitrilotriacetic acid (NTA), citric acid, fumaric acid, malic acid, maltol, tartaric acid, gluconic acid, glyceric acid, oxalic acid, phthalic acid, maleic acid, mandelic acid, malonic acid, lactic acid, salicylic acid, methyl salicylate, 5-sulfosalicylic acid, gallic acid, propyl gallate, pyrogallol, 8-hydroxyquinoline, cysteine, and the like, but not limited thereto.

The buffer includes disodium hydrogen phosphate (dibasic sodium phosphate), citric acid, sodium citrate hydrate, potassium citrate, acetic acid, sodium acetate, sodium carbonate, calcium carbonate, tricalcium phosphate, calcium lactate, glycine, maleic acid, malic acid, sodium glutamate, monosodium glutamate, sodium lactate, sodium phosphate, and the mixture thereof, but not limited thereto.

The cryoprotectant may be a sugar, a sugar alcohol, or a mixture thereof. The sugar may be one or more selected from the group consisting of lactose, maltose, sucrose, mannose, trehalose, xylose, fructose, and raffinose. The sugar alcohol may be one or more selected from the group consisting of mannitol, sorbitol, inositol, maltitol, xylitol, and lactitol. And also, the cryoprotectant may additionally include glycine, histidine, polyvinylpyrrolidone (PVP), and the like, but not limited thereto.

The organic solvent includes an alcohol such as ethanol (including anhydrous ethanol, fermented spirits and the like), methanol, acetone, di-acetone, octanol, isopropyl alcohol, lauryl alcohol, polyvinyl alcohol; and a glycol such as polyethylene glycol, ethylene glycol, propylene glycol, dipropylene glycol, butylene glycol, pentylene glycol, thioglycolic acid, but not limited thereto.

The oil includes vegetable oils, medium chain triglycerides (MCTs), cholesterol, glyceryl stearate, oleic acid, and the like, but not limited thereto. In an embodiment, the oil may be a vegetable oil and/or oleic acid. The vegetable oil may be selected from the group consisting of cottonseed oil, corn oil, sesame oil, soybean oil, olive oil, coconut oil, peanut oil, sunflower oil, safflower oil, almond oil, avocado oil, palm oil, palm kernel oil, babassu oil, beech nut oil, linseed oil, canola oil, and the combination thereof. In an embodiment, the vegetable oil may be soybean oil.

The aqueous solvent includes water for injection, sterile distilled water, saline, an aqueous dextrose solution, and an aqueous sucrose solution, and so on without limitation.

The pharmaceutical composition of the present invention is typically contained in a sealed and sterilized plastic or organic container. The container may be provided in the form of a defined volume such as an ampoule, a vial, a syringe or a cartridge, or may be provided in the form of a large volume such as a bag for injection or a bottle for injection.

In the pharmaceutical composition of the present invention, the compound of Formula 1 or pharmaceutically acceptable salt thereof may be administered in a therapeutically effective amount ranging from about 1 mg/kg to about 1,500 mg/kg per day, which may be changed according to patient's age, body weight, susceptibility, symptoms, dosage form, and the like. In an embodiment, the compound of Formula 1 or pharmaceutically acceptable salt thereof may be included in an amount ranging from 1 to 1,000 mg, preferably in an amount ranging from 1 to 500 mg, per unit formulation. And also, as mentioned in the above, the therapeutically effective amount of said bile acid or a pharmaceutically acceptable salt thereof may be appropriately determined through considering the weight ratio with the compound of Formula 1 or pharmaceutically acceptable salt thereof.

The present invention also comprises, within its scope, a method for inducing lipolysis or treating obesity in a mammal in need thereof, comprising administering to the mammal a therapeutically effective amount of the compound of Formula 1 or pharmaceutically acceptable salt thereof.

In the method of the present invention, the compound of Formula 1 may be one or more selected from the group consisting of:
1,2-didecanoyl-sn-glycero-3-phosphocholine,
1,2-dilauroyl-sn-glycero-3-phosphocholine,
1,2-dimyristoyl-sn-glycero-3-phosphocholine,
1,2-dipalmitoyl-sn-glycero-3-phosphocholine,
1-myristoyl-2-palmitoyl-sn-glycero-3-phosphocholine;
1-myristoyl-2-stearoyl-sn-glycero-3-phosphocholine,
1-palmitoyl-2-myristoyl-sn-glycero-3-phosphocholine;
1-palmitoyl-2-stearoyl-sn-glycero-3-phosphocholine,
1-stearoyl-2-myristoyl-sn-glycero-3-phosphocholine,
1-stearoyl-2-palmitoyl-sn-glycero-3-phosphocholine,
1,2-dierucoyl-sn-glycero-3-phosphocholine,
1,2-dioleoyl-sn-glycero-3-phosphocholine,
1-palmitoyl-2-oleoyl-sn-glycero-3-phosphocholine; and
1-stearoyl-2-oleoyl-sn-glycero-3-phosphocholine.

Preferably, the compound of Formula 1 may be one or more selected from the group consisting of:
1,2-dimyristoyl-sn-glycero-3-phosphocholine,
1,2-dipalmitoyl-sn-glycero-3-phosphocholine,
1-stearoyl-2-myristoyl-sn-glycero-3-phosphocholine,
1,2-didecanoyl-sn-glycero-3-phosphocholine,
1-palmitoyl-2-stearoyl-sn-glycero-3-phosphocholine; and
1,2-dilauroyl-sn-glycero-3-phosphocholine.

More preferably, the compound of Formula 1 may be 1,2-dimyristoyl-sn-glycero-3-phosphocholine.

The present invention also comprises, within its scope, a use of the compound of Formula 1 or pharmaceutically acceptable salt thereof for the manufacture of a medicament for inducing lipolysis or preventing or treating obesity.

In the use of the present invention, the compound of Formula 1 may be one or more selected from the group consisting of:
1,2-didecanoyl-sn-glycero-3-phosphocholine,
1,2-dilauroyl-sn-glycero-3-phosphocholine,
1,2-dimyristoyl-sn-glycero-3-phosphocholine,
1,2-dipalmitoyl-sn-glycero-3-phosphocholine,
1-myristoyl-2-palmitoyl-sn-glycero-3-phosphocholine;
1-myristoyl-2-stearoyl-sn-glycero-3-phosphocholine,
1-palmitoyl-2-myristoyl-sn-glycero-3-phosphocholine;
1-palmitoyl-2-stearoyl-sn-glycero-3-phosphocholine,
1-stearoyl-2-myristoyl-sn-glycero-3-phosphocholine,
1-stearoyl-2-palmitoyl-sn-glycero-3-phosphocholine;
1,2-dierucoyl-sn-glycero-3-phosphocholine,
1,2-dioleoyl-sn-glycero-3-phosphocholine,
1-palmitoyl-2-oleoyl-sn-glycero-3-phosphocholine; and
1-stearoyl-2-oleoyl-sn-glycero-3-phosphocholine.

Preferably, the compound of Formula 1 may be one or more selected from the group consisting of:
1,2-dimyristoyl-sn-glycero-3-phosphocholine,
1,2-dipalmitoyl-sn-glycero-3-phosphocholine,
1-stearoyl-2-myristoyl-sn-glycero-3-phosphocholine, 1,2-didecanoyl-sn-glycero-3-phosphocholine,
1-palmitoyl-2-stearoyl-sn-glycero-3-phosphocholine; and
1,2-dilauroyl-sn-glycero-3-phosphocholine.

More preferably, the compound of Formula 1 may be 1,2-dimyristoyl-sn-glycero-3-phosphocholine.

The present invention will be described in further detail with reference to the following examples and experimental examples. These examples and experimental examples are for illustrative purposes only and are not intended to limit the scope of the present invention.

Example 1: Preparation of Lyophilized Formulation

The lyophilized formulation in the form of lyophilized dry powder was prepared according to the components and amounts shown in Table 1. The amounts of Table 1 represent the weight (mg) of each component. Oleic acid, glycerin, cholesterol, and benzyl alcohol were dissolved in ethanol (50 ml) under stirring at 300 rpm. DMPC was dissolved in the resulting solution under heating at 70±10° C. to obtain a first solution.

The first solution was added to a solution of mannitol (62.5 mg) in water for injection (800 mL), followed by homogenizing with a high pressure homogenizer (Homogenizer Unidrive x1000D display, CAT GmbH, German) at 15,000 rpm for about 60 minutes to obtain an emulsion. The resulting emulsion was subject to sterile filtration with a membrane filter (PVDF 0.22 μm filter, Millipore, USA) and then lyophilized under the following conditions to obtain a formulation in the form of lyophilized dry powder. The lyophilized formulation was stored in a 10 ml vial.

|  | | Time | | |
| --- | --- | --- | --- | --- |
| Step | Temperature | RAMP | SOAK | Vacuum level |
| Pre-freezing | 5° C. | — | — | — |
| Freezing | −45° C. | 120 min | 180 min | — |
| First sublimation (Step 1) | −45° C. | 5 min | 5 min | 13 Pa |
| First sublimation (Step 2) | −15° C. | 150 min | 420 min | 13 Pa |
| First sublimation (Step 3) | 10° C. | 300 min | 3800 min | 13 Pa |
| Second drying (Step 1) | 20° C. | 150 min | 360 min | 13 Pa |
| Second drying (Step 2) | 30° C. | 150 min | 420 min | 5 Pa |

Examples 2 to 18: Preparation of Lyophilized Formulations

The lyophilized formulations in the form of lyophilized dry powder were prepared according to the components and amounts shown in Tables 1 and 2. The amounts of Tables 1 and 2 represent the weight (mg) of each component. The first solutions were prepared in accordance with the same procedures as in Example 1, using DMPC or the other phosphocholine derivatives.

In separate vessels, disodium hydrogen phosphate, sodium chloride and sodium hydroxide were dissolved in water for injection (150 ml) under stirring at 300 rpm. In the resulting solution, was the bile acid or a salt thereof dissolved to obtain the respective second solutions.

The first solution (50 mL) and the second solution (150 mL) were mixed with each other under heating at 70±10° C., followed by homogenizing with a high pressure homogenizer (Homogenizer Unidrive x1000D display, CAT GmbH, German) at 10,000 rpm for about 30 minutes to obtain the respective emulsions. The resulting emulsions were added to a solution of mannitol (62.9 mg) in water for injection (800 mL) and then homogenized with a high pressure homogenizer (Homogenizer Unidrive x1000D display, CAT GmbH, German) at 15,000 rpm for about 60 minutes to obtain the respective emulsions. The resulting emulsions were subject to sterile filtration with a membrane filter (PVDF 0.22 μm filter, Millipore, USA) and then lyophilized under the same conditions as in Example 1 to obtain formulations in the form of lyophilized dry powder. The lyophilized formulations were stored in a 10 ml vial.

TABLE 1

|  |  | Example | | | | | | | |
| --- | --- | --- | --- | --- | --- | --- | --- | --- | --- |
|  |  | 1 | 2 | 3 | 4 | 5 | 6 | 7 | 8 |
| First solution (in oily phase) | DMPC | 150 | 150 | 150 | 150 | 150 | 200 | 100 | 100 |
|  | DPPC | — | — | — | — | — | — | — | — |
|  | SMPC | — | — | — | — | — | — | — | — |
|  | DDPC | — | — | — | — | — | — | — | — |
|  | PSPC | — | — | — | — | — | — | — | — |
|  | DLPC | — | — | — | — | — | — | — | — |
|  | Glycerin | 1 | 1 | 1 | 1 | 1 | 1 | 1 | 1 |
|  | Benzyl alcohol | 9 | 9 | 9 | 9 | 9 | 9 | 9 | 9 |
|  | Oleic acid | 1.5 | 1.5 | 1.5 | 1.5 | 1.5 | 1.5 | 1.5 | 1.5 |
|  | Cholesterol | 0.7 | 0.7 | 0.7 | 0.7 | 0.7 | 0.7 | 0.7 | 0.7 |
|  | Ethanol (ml) | 50 | 50 | 50 | 50 | 50 | 50 | 50 | 50 |
| Second solution (in aqueous phase) | Sodium deoxycholate | — | — | — | — | 15.4 | — | — | — |
|  | Sodium taurocholate | — | 20 | — | — | — | 50 | 20 | 10 |
|  | Glycocholic acid | — | — | 17.3 | — | — | — | — | — |
|  | Tauroursodeoxycholic acid | — | — | — | 18.6 | — | — | — | — |
|  | Disodium hydrogen phosphate | — | 1.4 | 1.4 | 1.4 | 1.4 | 1.4 | 1.4 | 1.4 |
|  | Sodium chloride | — | 4.4 | 4.4 | 4.4 | 4.4 | 4.4 | 4.4 | 4.4 |
|  | Sodium hydroxide | — | 1.4 | 1.4 | 1.4 | 1.4 | 1.4 | 1.4 | 1.4 |

TABLE 1-continued

| | Example | | | | | | | |
|---|---|---|---|---|---|---|---|---|
| | 1 | 2 | 3 | 4 | 5 | 6 | 7 | 8 |
| Water for injection (containing 62.9 mg of mannitol, ml) | 800 | 800 | 800 | 800 | 800 | 800 | 800 | 800 |
| Phosphocholine derivative: bile acid (weight ratio) | — | 15:2 | 15:2 | 15:2 | 15:2 | 4:1 | 5:1 | 10:1 |

TABLE 2

| | | Example | | | | | | | | | |
|---|---|---|---|---|---|---|---|---|---|---|---|
| | | 9 | 10 | 11 | 12 | 13 | 14 | 15 | 16 | 17 | 18 |
| First solution (in oily phase) | DMPC | 150 | 120 | 100 | 200 | 120 | — | — | — | — | — |
| | DPPC | — | — | — | — | — | 139.3 | — | — | — | — |
| | SMPC | — | — | — | — | — | — | 139.3 | — | — | — |
| | DDPC | — | — | — | — | — | — | — | 107.4 | — | — |
| | PSPC | — | — | — | — | — | — | — | — | 144.7 | — |
| | DLPC | — | — | — | — | — | — | — | — | — | 118.0 |
| | Glycerin | 1 | 1 | 1 | 1 | 1 | 1 | 1 | 1 | 1 | 1 |
| | Benzyl alcohol | 9 | 9 | 9 | 9 | 9 | 9 | 9 | 9 | 9 | 9 |
| | Oleic acid | 1.5 | 1.5 | 1.5 | 1.5 | 1.5 | 1.5 | 1.5 | 1.5 | 1.5 | 1.5 |
| | Cholesterol | 0.7 | 0.7 | 0.7 | 0.7 | 0.7 | 0.7 | 0.7 | 0.7 | 0.7 | 0.7 |
| | Ethanol (ml) | 50 | 50 | 50 | 50 | 50 | 50 | 50 | 50 | 50 | 50 |
| Second solution (in aqueous phase) | Sodium deoxycholate | — | — | — | — | — | — | — | — | — | — |
| | Sodium taurocholate | 70 | 20 | 100 | 150 | 40 | 20 | 20 | 20 | 20 | 20 |
| | Glycocholic acid | — | — | — | — | — | — | — | — | — | — |
| | Tauroursodeoxycholic acid | — | — | — | — | — | — | — | — | — | — |
| | Disodium hydrogen phosphate | 1.4 | 1.4 | 1.4 | 1.4 | 1.4 | 1.4 | 1.4 | 1.4 | 1.4 | 1.4 |
| | Sodium chloride | 4.4 | 4.4 | 4.4 | 4.4 | 4.4 | 4.4 | 4.4 | 4.4 | 4.4 | 4.4 |
| | Sodium hydroxide | 1.4 | 1.4 | 1.4 | 1.4 | 1.4 | 1.4 | 1.4 | 1.4 | 1.4 | 1.4 |
| Water for injection (containing 62.9 mg of mannitol, ml) | | 800 | 800 | 800 | 800 | 800 | 800 | 800 | 800 | 800 | 800 |
| Phosphocholine derivative: bile acid (weight ratio) | | 2.5:1 | 6:1 | 1:1 | 4:3 | 3:1 | 15:2 | 15:2 | 15:2 | 15:2 | 15:2 |

Example 19: Preparation of Solution

The formulation in the form of solution was prepared according to the components and amounts shown in Table 3. The amounts of Table 3 represent the weight (mg) of each component. Benzyl alcohol and Tween 80 were dissolved in water for injection (7-8 ml) heated to about 30° C. DMPC was dissolved in the resulting solution under stirring at 300 rpm for 1 hour. After adjusting the pH by dissolving disodium hydrogen phosphate, sodium chloride, and sodium hydroxide in the resulting solution under heating at about 30° C., the final volume of the solution was adjusted to 10 ml with water for injection. The resulting solution was subject to sterile filtration with a membrane filter (PVDF 0.22 μm filter, Millipore, USA) and then filled into a vial.

Examples 20 to 36: Preparation of Solutions

The formulations in the form of solution were prepared according to the components and amounts shown in Tables 3 and 4. The amounts of Tables 3 and 4 represent the weight (mg) of each component. Benzyl alcohol and Tween 80 were dissolved in water for injection (7-8 ml) which had been heated to about 30° C. Each bile acid or a salt thereof was dissolved in the solution under stirring at 300 rpm for 1 hour (the second solutions). DMPC or the other phosphocholine derivative was dissolved in each second solution under stirring at 300 rpm for 1 hour, while heating the second solution at about 30° C. After adjusting the pH by dissolving disodium hydrogen phosphate, sodium chloride, and sodium hydroxide, the final volume of each solution was adjusted to 10 ml with water for injection. The resulting each solution was subject to sterile filtration with a membrane filter (PVDF 0.22 μm filter, Millipore, USA) and then filled into a vial.

TABLE 3

|  |  | Example |  |  |  |  |  |  |  |
|---|---|---|---|---|---|---|---|---|---|
|  |  | 19 | 20 | 21 | 22 | 23 | 24 | 25 | 26 |
| First solution | DMPC | 150 | 150 | 150 | 150 | 150 | 200 | 100 | 100 |
|  | DPPC | — | — | — | — | — | — | — | — |
|  | SMPC | — | — | — | — | — | — | — | — |
|  | DDPC | — | — | — | — | — | — | — | — |
|  | PSPC | — | — | — | — | — | — | — | — |
|  | DLPC | — | — | — | — | — | — | — | — |
|  | Disodium hydrogen phosphate | 1.4 | 1.4 | 1.4 | 1.4 | 1.4 | 1.4 | 1.4 | 1.4 |
|  | Sodium chloride | 4.4 | 4.4 | 4.4 | 4.4 | 4.4 | 4.4 | 4.4 | 4.4 |
|  | Sodium hydroxide | 1.4 | 1.4 | 1.4 | 1.4 | 1.4 | 1.4 | 1.4 | 1.4 |
| Second solution | Sodium deoxycholate | — | — | — | — | 15.4 | — | — | — |
|  | Sodium taurocholate | — | 20 | — | — | — | 50 | 20 | 10 |
|  | Glycocholic acid | — | — | 17.3 | — | — | — | — | — |
|  | Tauroursodeoxycholic acid | — | — | — | 18.6 | — | — | — | — |
|  | Benzyl alcohol | 9 | 9 | 9 | 9 | 9 | 9 | 9 | 9 |
|  | Tween 80 | 27.5 | 27.5 | 27.5 | 27.5 | 27.5 | 27.5 | 27.5 | 27.5 |
|  | Water for injection (final volume, ml) | 10 | 10 | 10 | 10 | 10 | 10 | 10 | 10 |
|  | Phosphocholine derivative: bile acid (weight ratio) | — | 15:2 | 15:2 | 15:2 | 15:2 | 4:1 | 5:1 | 10:1 |

TABLE 4

|  |  | Example |  |  |  |  |  |  |  |  |  |
|---|---|---|---|---|---|---|---|---|---|---|---|
|  |  | 27 | 28 | 29 | 30 | 31 | 32 | 33 | 34 | 35 | 36 |
| First solution | DMPC | 150 | 120 | 100 | 200 | 120 | — | — | — | — | — |
|  | DPPC | — | — | — | — | — | 139.3 | — | — | — | — |
|  | SMPC | — | — | — | — | — | — | 139.3 | — | — | — |
|  | DDPC | — | — | — | — | — | — | — | 107.4 | — | — |
|  | PSPC | — | — | — | — | — | — | — | — | 144.7 | — |
|  | DLPC | — | — | — | — | — | — | — | — | — | 118.0 |
|  | Disodium hydrogen phosphate | 1.4 | 1.4 | 1.4 | 1.4 | 1.4 | 1.4 | 1.4 | 1.4 | 1.4 | 1.4 |
|  | Sodium chloride | 4.4 | 4.4 | 4.4 | 4.4 | 4.4 | 4.4 | 4.4 | 4.4 | 4.4 | 4.4 |
|  | Sodium hydroxide | 1.4 | 1.4 | 1.4 | 1.4 | 1.4 | 1.4 | 1.4 | 1.4 | 1.4 | 1.4 |
| Second solution | Sodium deoxycholate | — | — | — | — | — | — | — | — | — | — |
|  | Sodium taurocholate | 70 | 20 | 100 | 150 | 40 | 20 | 20 | 20 | 20 | 20 |
|  | Glycocholic acid | — | — | — | — | — | — | — | — | — | — |
|  | Tauroursodeoxycholic acid | — | — | — | — | — | — | — | — | — | — |
|  | Benzyl alcohol | 9 | 9 | 9 | 9 | 9 | 9 | 9 | 9 | 9 | 9 |
|  | Tween 80 | 27.5 | 27.5 | 27.5 | 27.5 | 27.5 | 27.5 | 27.5 | 27.5 | 27.5 | 27.5 |
|  | Water for injection (final volume, ml) | 10 | 10 | 10 | 10 | 10 | 10 | 10 | 10 | 10 | 10 |
|  | Phosphocholine derivative: bile acid (weight ratio) | 2.5:1 | 6:1 | 1:1 | 4:3 | 3:1 | 15:2 | 15:2 | 15:2 | 15:2 | 15:2 |

Comparative Example 1

The solution containing phosphatidylcholine was prepared in accordance with the same procedures as in Example 19, except that phosphatidylcholine (150 mg) was used instead of DMPC.

Comparative Example 2

The solution containing phosphatidylcholine and sodium deoxycholate was prepared in accordance with the same procedures as in Example 20, except that phosphatidylcholine (150 mg) and sodium deoxycholate (20 mg) were used instead of DMPC and sodium taurocholate, respectively.

Experimental Example 1: Measurement of Lipolytic Activities

1. Preparation of Animal Models and Administration

Sprague-Dawley rats (4 weeks old, Orient Bio Inc. (Seongnam, Republic of Korea)) were fed a high-fat diet (D12492, 5% calories from fats, 20% calories from proteins, and 35% calories from carbohydrates, RESEARCH DIET Inc., New Brunswick, N.J., USA) for 9 weeks. The rats were maintained at 20.0~24.0° C. under the condition of 40~60% relative humidity with a 12 hour light/dark cycle and water was offered ad libitum. The weights of the rats were monitored so as to obtain high-fat rats (fed for 9 weeks, 13 weeks old in total). The average weights of the rats in the respective groups (13 weeks old in total, n=10) are shown in Table 5.

Each 0.2 mL of the vehicle containing no active ingredient, the formulations of Examples 1 to 36, and the formulations of Comparative Examples 1 and 2 was subcutaneously injected into the left groin of the high-fat rats of the respective groups (n=10) once a week for 4 weeks. The formulations of Examples 1 to 18 were subcutaneously injected after dissolving each lyophilized powder in water for injection (10 mL).

TABLE 5

| Group (n = 10) | Average weight (9th week old, 13 weeks old) | Formulations administered |
|---|---|---|
| Group 1 | 691.90 g | Example 1 |
| Group 2 | 682.77 g | Example 2 |
| Group 3 | 680.71 g | Example 3 |
| Group 4 | 685.40 g | Example 4 |
| Group 5 | 683.20 g | Example 5 |
| Group 6 | 684.10 g | Example 6 |
| Group 7 | 681.50 g | Example 7 |
| Group 8 | 682.50 g | Example 8 |
| Group 9 | 707.02 g | Example 9 |
| Group 10 | 700.86 g | Example 10 |
| Group 11 | 686.95 g | Example 11 |
| Group 12 | 682.94 g | Example 12 |
| Group 13 | 698.25 g | Example 13 |
| Group 14 | 683.30 g | Example 14 |
| Group 15 | 701.15 g | Example 15 |
| Group 16 | 693.26 g | Example 16 |
| Group 17 | 688.22 g | Example 17 |
| Group 18 | 689.10 g | Example 18 |
| Group 19 | 688.40 g | Example 19 |
| Group 20 | 690.54 g | Example 20 |
| Group 21 | 690.91 g | Example 21 |
| Group 22 | 688.71 g | Example 22 |
| Group 23 | 690.65 g | Example 23 |
| Group 24 | 683.74 g | Example 24 |
| Group 25 | 685.75 g | Example 25 |
| Group 26 | 690.48 g | Example 26 |
| Group 27 | 689.58 g | Example 27 |
| Group 28 | 688.74 g | Example 28 |
| Group 29 | 687.15 g | Example 29 |
| Group 30 | 688.97 g | Example 30 |
| Group 31 | 687.65 g | Example 31 |
| Group 32 | 692.85 g | Example 32 |
| Group 33 | 698.55 g | Example 33 |
| Group 34 | 697.40 g | Example 34 |
| Group 35 | 694.15 g | Example 35 |
| Group 36 | 699.30 g | Example 36 |
| Group 37 | 688.97 g | Comparative Example 1 |
| Group 38 | 687.65 g | Comparative Example 2 |
| Group 39 | 704.84 g | Vehicle |

2. Evaluation on Side Effects and Lipolytic Effects

After 2 weeks of recovery from the administration for 4 weeks, the rats in each group were sacrificed, followed by observation for inflammation and necrosis; measurement of fat reduction rate at the administration site; evaluation of side effects such as inflammation through Hematoxylin and Eosin staining; and measurement of lipolytic effects through Oil Red O reaction.

(1) Observation of Inflammation and Necrosis

After 2 weeks of recovery from the administration for 4 weeks, the rats in each group were sacrificed and then the subcutaneous injection sites were observed with the naked eyes and tested tactilely. As the results thereof, in the groups administered with the formulations of the present invention, neither necrosis nor inflammation was observed at the injection sites; and also no firm part was touched in the tactile test. However, in the groups administered with the formulations of Comparative Examples 1 and 2, necrosis and inflammation were observed at the injection sites with the naked eyes; and also severely firm changes were touched in the tactile test.

(2) Measurement of Fat Reduction Rate at the Administration Site

After 2 weeks of recovery from the administration for 4 weeks, the rats in each group were sacrificed and the tissue autopsy thereof was performed. The subcutaneous tissues derived both from the right groin and from the left groin (the administration site) were observed with the naked eyes so as to confirm any abnormal findings; and the photographs thereof were taken. And then, the tissues were taken therefrom and weighed. The relative weight and the reduction rate were calculated according to the following formula. The results thereof are shown in Table 6 below and the photographs thereof are shown in FIG. 1.

Relative weight (g)=the weight of fat in the groin (g)/body weight (g)

Reduction rate (%)=[1−(left (g)/right (g))]×100%

TABLE 6

| | Weight of fat in the groin (g) | | Relative weight (g) | | |
|---|---|---|---|---|---|
| | Left (the administration site) | Right | Left (the administration site) | Right | Reduction rate (%) |
| Example 1 | 4.0052 | 5.1944 | 0.0057 | 0.0075 | 22.89% |
| Example 2 | 3.5511 | 4.6151 | 0.0051 | 0.0068 | 23.05% |
| Example 3 | 3.7515 | 4.8670 | 0.0054 | 0.0071 | 22.92% |
| Example 4 | 3.7748 | 4.8842 | 0.0055 | 0.0071 | 22.71% |
| Example 5 | 3.7185 | 4.8186 | 0.0054 | 0.0071 | 22.83% |
| Example 6 | 3.3555 | 4.4451 | 0.0050 | 0.0065 | 24.51% |
| Example 7 | 3.7388 | 4.7849 | 0.0055 | 0.0070 | 21.86% |
| Example 8 | 3.4773 | 4.4146 | 0.0051 | 0.0065 | 21.23% |
| Example 9 | 3.7266 | 4.8236 | 0.0054 | 0.0068 | 22.74% |
| Example 10 | 3.8009 | 4.8186 | 0.0054 | 0.0069 | 21.12% |
| Example 11 | 3.8482 | 4.8467 | 0.0058 | 0.0071 | 20.60% |
| Example 12 | 3.7877 | 4.9839 | 0.0058 | 0.0073 | 24.00% |
| Example 13 | 4.2999 | 5.4665 | 0.0065 | 0.0078 | 21.34% |
| Example 14 | 3.7844 | 4.8632 | 0.0056 | 0.0071 | 22.18% |
| Example 15 | 4.0191 | 5.1944 | 0.0057 | 0.0074 | 22.63% |

TABLE 6-continued

|  | Weight of fat in the groin (g) | | Relative weight (g) | | |
|---|---|---|---|---|---|
|  | Left (the administration site) | Right | Left (the administration site) | Right | Reduction rate (%) |
| Example 16 | 3.7736 | 4.8670 | 0.0054 | 0.0070 | 22.47% |
| Example 17 | 3.8523 | 4.9530 | 0.0056 | 0.0072 | 22.22% |
| Example 18 | 3.5764 | 4.6151 | 0.0052 | 0.0067 | 22.51% |
| Example 19 | 3.6078 | 4.6151 | 0.0051 | 0.0067 | 21.83% |
| Example 20 | 4.0087 | 5.1944 | 0.0057 | 0.0075 | 22.83% |
| Example 21 | 3.9466 | 5.0512 | 0.0056 | 0.0073 | 21.87% |
| Example 22 | 3.9659 | 5.0706 | 0.0058 | 0.0074 | 21.79% |
| Example 23 | 4.0636 | 5.2003 | 0.0059 | 0.0075 | 21.86% |
| Example 24 | 3.9815 | 5.2360 | 0.0060 | 0.0077 | 23.96% |
| Example 25 | 4.1056 | 5.1575 | 0.0060 | 0.0075 | 20.40% |
| Example 26 | 3.9893 | 4.9960 | 0.0058 | 0.0072 | 20.15% |
| Example 27 | 3.8761 | 4.9599 | 0.0057 | 0.0072 | 21.85% |
| Example 28 | 3.9919 | 5.0510 | 0.0059 | 0.0073 | 20.97% |
| Example 29 | 3.9212 | 4.8866 | 0.0059 | 0.0071 | 19.76% |
| Example 30 | 3.8077 | 5.0005 | 0.0059 | 0.0073 | 23.85% |
| Example 30 | 3.9543 | 4.9999 | 0.0060 | 0.0073 | 20.91% |
| Example 32 | 3.9144 | 4.9891 | 0.0057 | 0.0072 | 21.54% |
| Example 33 | 3.8763 | 4.9087 | 0.0055 | 0.0070 | 21.03% |
| Example 34 | 3.9013 | 4.9886 | 0.0056 | 0.0072 | 21.80% |
| Example 35 | 3.9977 | 5.1201 | 0.0059 | 0.0074 | 21.92% |
| Example 36 | 3.9711 | 5.0807 | 0.0058 | 0.0073 | 21.84% |
| Comparative Example 1 | 4.8875 | 5.0210 | 0.0070 | 0.0073 | 4.03% |
| Comparative Example 2 | 4.8991 | 5.0708 | 0.0070 | 0.0074 | 5.37% |
| Vehicle | 4.8814 | 4.9864 | 0.0069 | 0.0071 | 2.11% |

Figure 2:
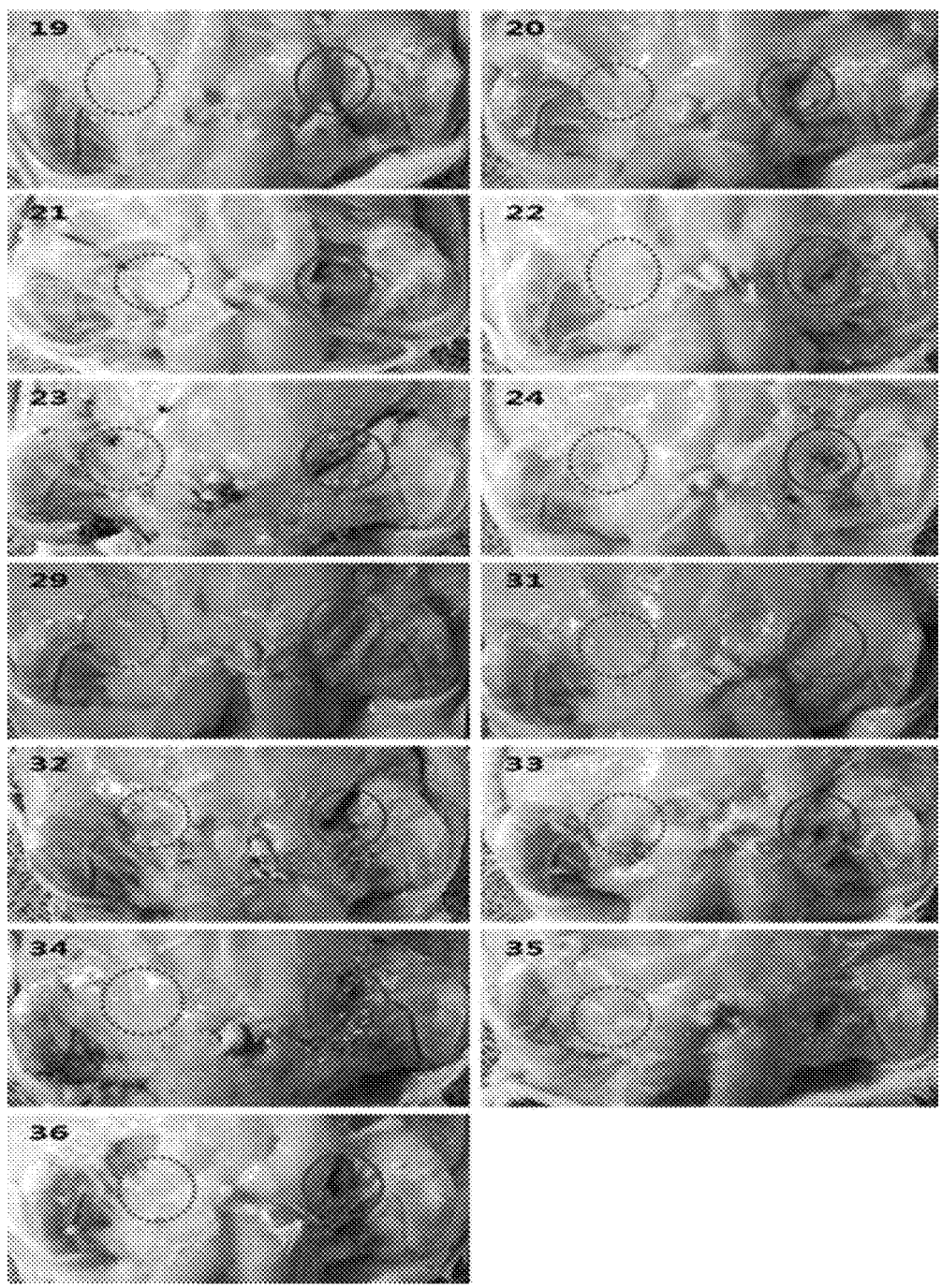

As shown in Table 6, it can be confirmed that the groups administered with the formulations of the present invention showed remarkable decreases in both the organ weight and the relative weight of the administration site, thereby exhibiting excellent lipolytic activities. And also, as shown in FIGS. 1 and 2, it can be confirmed that the lipolytic activities at the administration site (dark circle) are remarkably superior as compared with those at the non-administration site (dotted circle), when observed with the naked eye.

(3) Measurement of Side Effects through Hematoxylin and Eosin Staining

Figure 3:
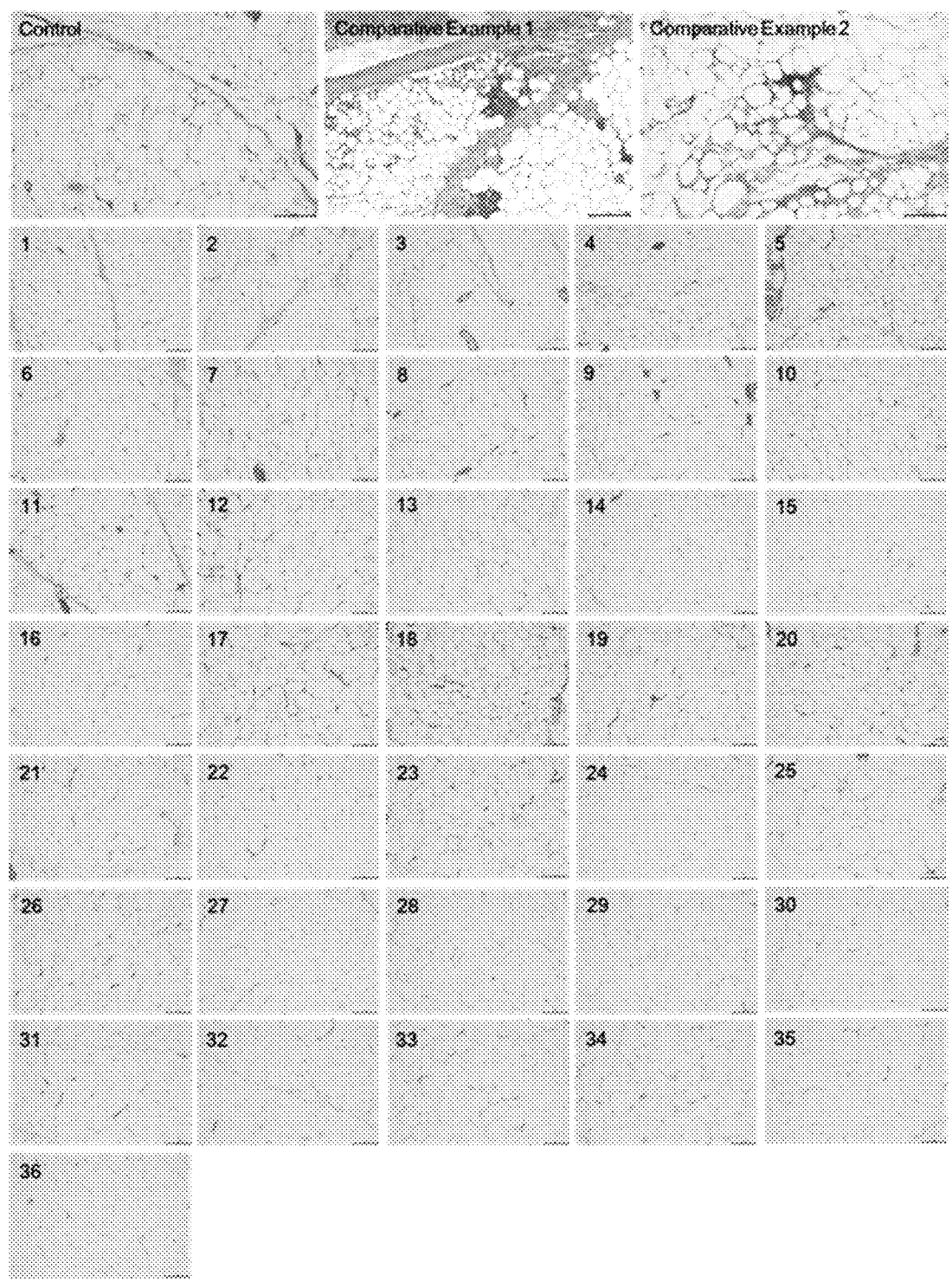
FIG. 3 shows the results obtained from measuring side effects such as inflammation, through hematoxylin and eosin staining of the subcutaneous fats taken from the rats administered with the formulations of the present invention, the formulations of Comparative Examples, and the vehicle.

After the abdomen and the groin of the sacrificed rats were dissected, each subcutaneous fat was rapidly taken and then immersed in a 10% neutral buffered formaldehyde solution for fixation. After washing with water and dehydrating, the cells were treated with a paraffin solution to make a paraffin block. Each paraffin block was cut to a thickness of 4-5 µm, stained with hematoxylin and eosin, and then observed with an optical microscope. As the results thereof, as shown in FIG. 3, mostly intact adipocytes were observed in the groups administered with the formulations of the present invention, whereas the findings of inflammatory reaction were observed in the groups administered with the formulations of Comparative Examples 1 and 2.

(4) Measurement of Lipolytic Effects through Oil Red O Reaction

Figure 4:
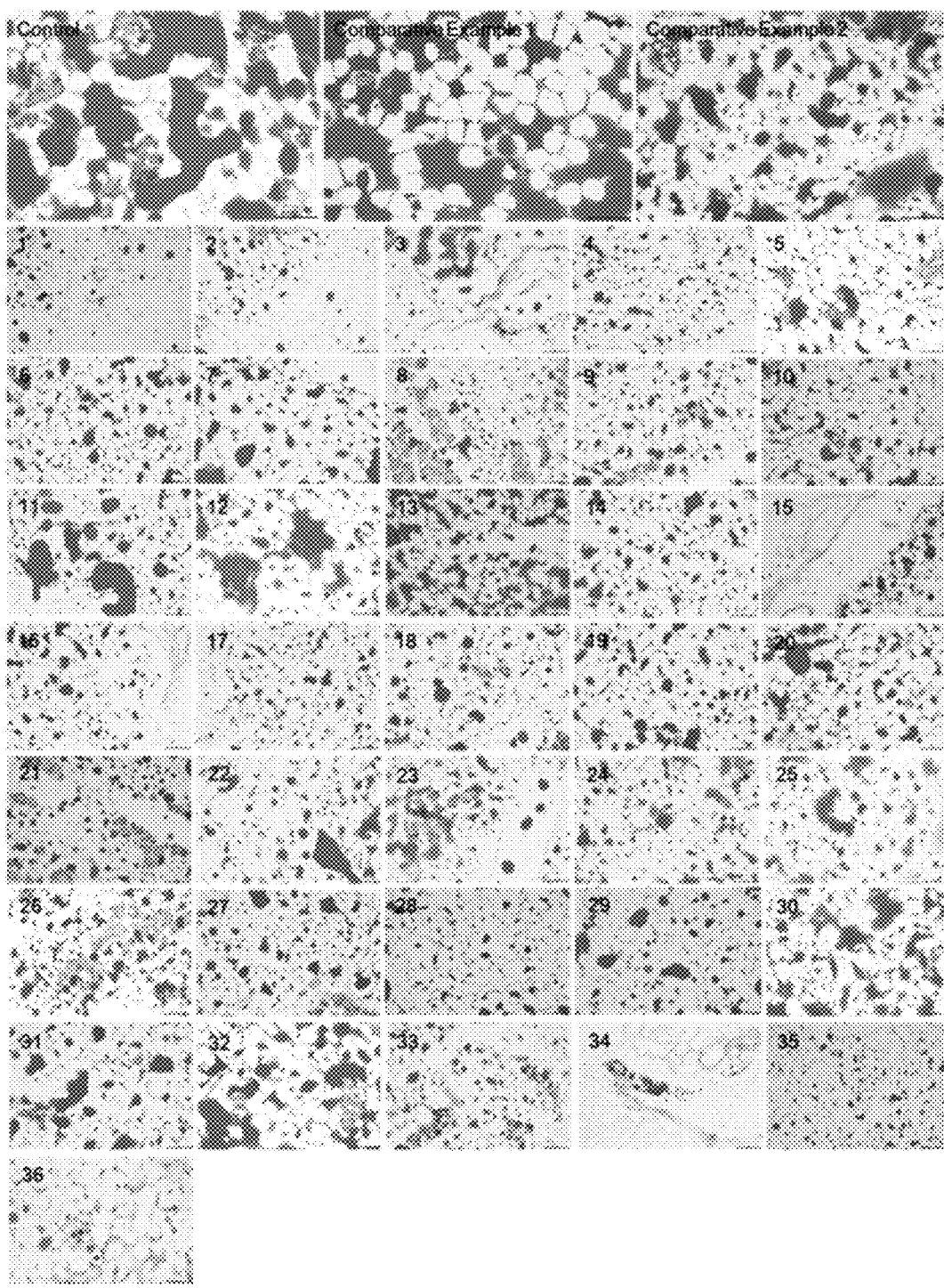
FIG. 4 shows the results obtained from measuring the uniformity of the lipolytic activities through Oil Red O reaction of the subcutaneous fats taken from the rats administered with the formulations of the present invention, the formulations of Comparative Examples, and the vehicle.
Figure 5:
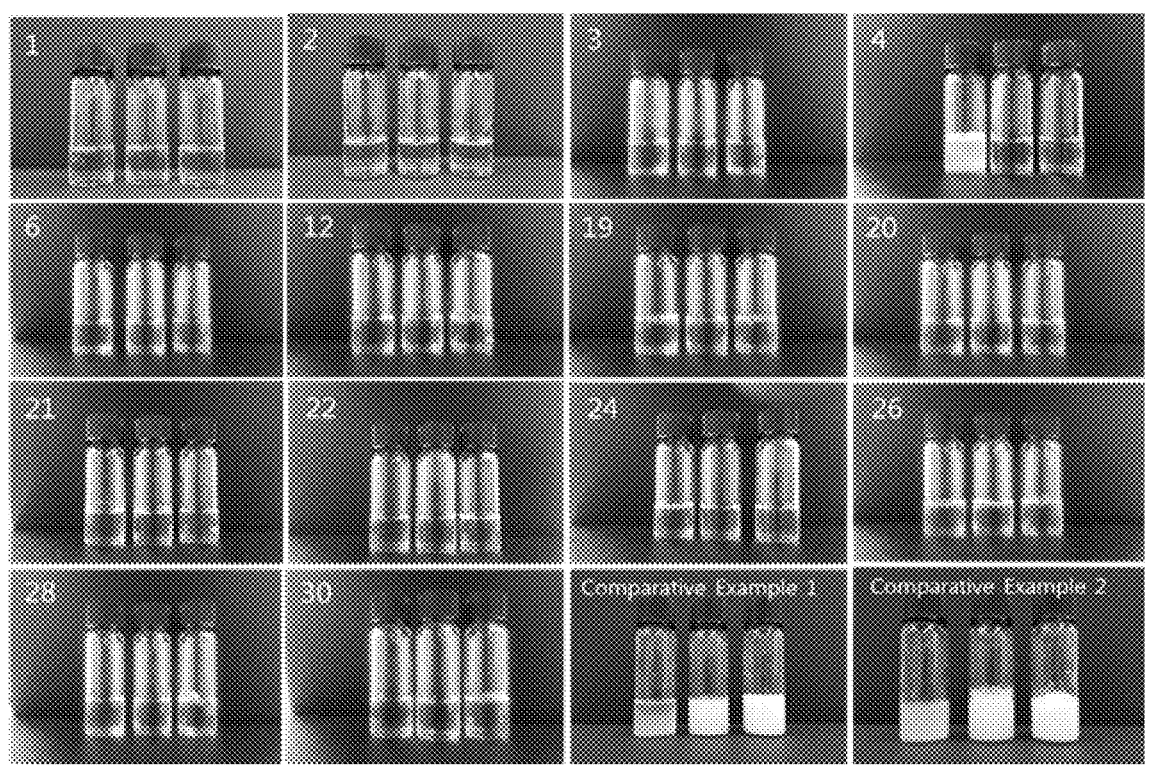
FIG. 5 shows the results obtained from evaluating the stabilities of the formulations of the present invention and the formulations of Comparative Examples after storing at room temperature for 7 days and 30 days. The first, second and third samples of each panel exhibit the appearances at the time of preparation, after storage at room temperature for 7 days, and after the storage at room temperature for 30 days, respectively.

After the abdomen and the groin of the sacrificed rats were dissected, each subcutaneous fat was rapidly taken and then the fat tissues in the groin were fixed with a 4% formaldehyde solution for 24 hours. After dehydrating with a 30% sucrose solution for 24 hours, the OCT-embedding cryostats were prepared using cryotome (FSE Cryostats, Thermo Scientific). After slides were prepared in a thickness of 10 µm, adipose tissues were stained with an Oil Red O (Lipid Stain) staining kit (product number: ab150678, Abcam, USA) and the levels of lipolysis were observed with an optical microscope. As the results thereof, as shown in FIG. 4, it can be confirmed that the groups administered with the formulations of the present invention exhibited uniform fat distribution, while the groups administered with the formulations of Comparative Examples 1 and 2 showed aggregated fats, i.e., non-uniform fat distribution. Therefore, it can be confirmed that the formulations of the present invention have a uniform lipolytic activity at the administration site, while the formulations of Comparative Examples 1 and 2 cannot achieve uniform lipolysis Experimental Example 2. Stability Test The formulations of Examples 1 to 4, 6, 12, 19 to 22, 24, 26, 28, and 30 and Comparative Examples 1 and 2 were stored at room temperature for 7 days and 30 days. The formulations of Examples 1 to 4, 6 and 12 were stored after dissolving in water for injection (10 ml). The results for the initial preparation of each formulation, storage at room temperature for 7 days, and storage at room temperature for 30 days are shown in FIG. 5. From the results of FIG. 5, it can be seen that the formulations of the present invention have excellent stability.

The invention claimed is:

1. A method for treating localized fat deposits in a subject in need thereof, comprising topically administering to the subject a pharmaceutical composition comprising a therapeutically effective amount of a phosphocholine derivative or pharmaceutically acceptable salt thereof,
   wherein the phosphocholine derivative is selected from the group consisting of
      1,2-dimyristoyl-sn-glycero-3-phosphocholine;
      1,2-dipalmitoyl-sn-glycero-3-phosphocholine;
      1-stearoyl-2-myristoyl-sn-glycero-3-phosphocholine;

1,2-didecanoyl-sn-glycero-3-phosphocholine; and
1-palmitoyl-2-stearoyl-sn-glycero-3-phosphocholine,
and wherein the pharmaceutical composition is a formulation for topical administration selected from the group consisting of a formulation for transdermal administration, a formulation for subcutaneous administration, a formulation for intramuscular administration, and a formulation for intraperitoneal administration.

2. The method according to claim 1, wherein the phosphocholine derivative is 1,2-dimyristoyl-sn-glycero-3-phosphocholine.

3. The method according to claim 1, wherein the pharmaceutical composition further comprises a therapeutically effective amount of bile acid or pharmaceutically acceptable salt thereof.

4. The method according to claim 3, wherein the bile acid or pharmaceutically acceptable salt thereof is one or more selected from the group consisting of cholic acid, glycocholic acid, glycodeoxycholic acid, deoxycholic acid, taurocholic acid, ursodeoxycholic acid, tauroursodeoxycholic acid, taurodeoxycholic acid, chenodeoxycholic acid, glycoursodeoxycholic acid, sodium deoxycholate, and sodium taurocholate.

5. The method according to claim 3, wherein the bile acid or pharmaceutically acceptable salt thereof is one or more selected from the group consisting of glycocholic acid, deoxycholic acid, taurocholic acid, tauroursodeoxycholic acid, glycoursodeoxycholic acid, sodium deoxycholate, and sodium taurocholate.

6. The method according to claim 3, wherein the phosphocholine derivative or pharmaceutically acceptable salt thereof and the bile acid or pharmaceutically acceptable salt thereof are in a weight ratio of from 0.5:1 to 40:1.

7. The method according to claim 1, wherein the formulation for topical administration is a liquid formulation or a dry powder formulation.

8. The method according to claim 1, wherein the formulation for topical administration is a solution, an emulsion, or a lyophilized powder.

9. The method according to claim 1, wherein the formulation for topical administration comprises one or more pharmaceutically acceptable excipient(s) selected from the group consisting of a pH controlling agent, an isotonic agent, a surfactant, a stabilizer, a preservative, a chelating agent, a buffer, and a cryoprotectant; and one or more pharmaceutically acceptable carriers selected from the group consisting of an oil, an organic solvent, and an aqueous solvent.

* * * * *